United States Patent [19]

Murata

[11] Patent Number: 4,872,446
[45] Date of Patent: Oct. 10, 1989

[54] ENDOSCOPE WITH COLOR CORRECTING MECHANISM

[75] Inventor: Moriyoshi Murata, Tochigi, Japan

[73] Assignee: Kabushiki Kaisha Toshiba, Kawasaki, Japan

[21] Appl. No.: 245,240

[22] Filed: Sep. 16, 1988

[30] Foreign Application Priority Data

Sep. 25, 1987 [JP] Japan ................................. 62-238829

[51] Int. Cl.⁴ .............................................. A61B 1/06
[52] U.S. Cl. .......................................... 128/6; 358/98
[58] Field of Search .......................... 128/4, 6; 358/98

[56] References Cited

U.S. PATENT DOCUMENTS 4,146,019  3/1979  Bass et al. ............................... 128/6
4,716,457 12/1987  Matsuo ................................... 358/98

Primary Examiner—William H. Grieb
Attorney, Agent, or Firm—Foley & Lardner, Schwartz, Jeffery, Schwaab, Mack, Blumenthal & Evans

[57] ABSTRACT

An endoscope which can facilitate color corrections inside an internal organ is disclosed. The endoscope includes colored sheets on a side wall of a scope which can be viewed by an imaging device so that they can be used for color corrections regardless of where the scope is located. Colored sheets can also be used to verify correspondence between displayed colors and actual colors.

11 Claims, 2 Drawing Sheets

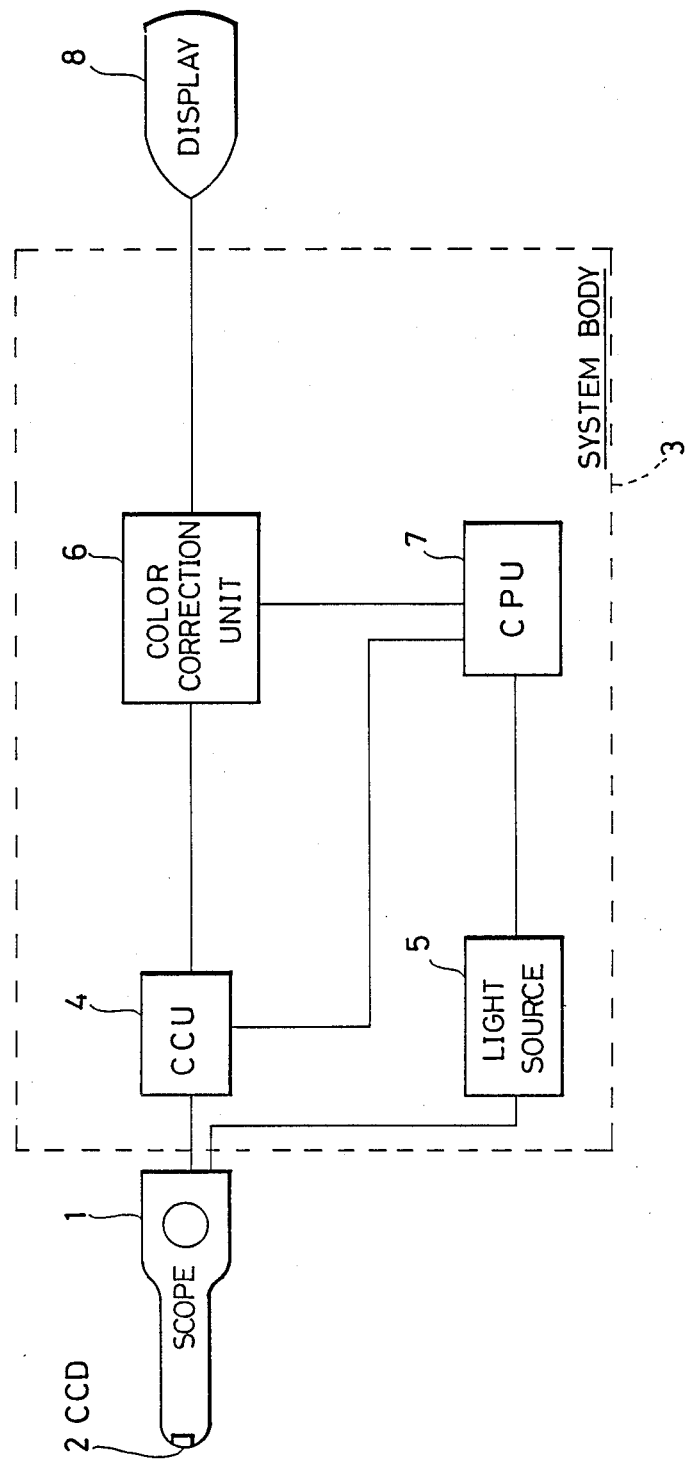

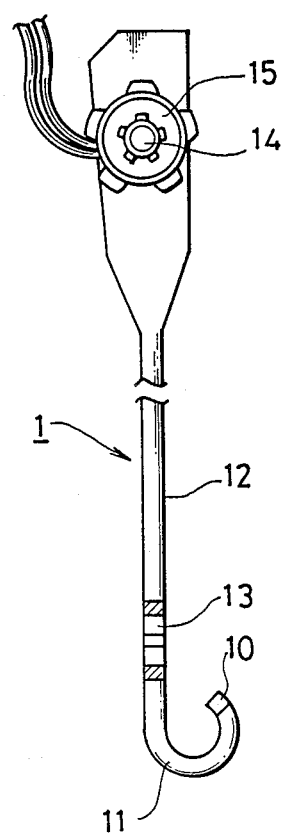
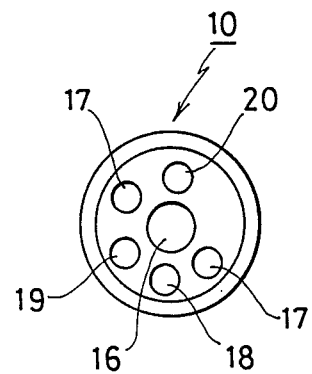
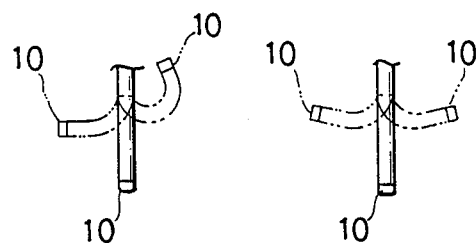

ENDOSCOPE WITH COLOR CORRECTING MECHANISM

BACKGROUND OF THE INVENTION

1. Field of the Invention

The present invention relates to an endoscope including a mechanism to facilitate color corrections required for reproductions of natural or desired colors of an imaged object on a display and a mechanism to facilitate verifications of correspondence between actual colors and displayed colors.

2. Description of the Prior Art

In a clinical diagnosis using an endoscope, the color qualities of displayed images provide valuable guidances for distinguishing abnormal parts from normal parts, and for judging the severity of diseases. It is therefore crucially important for an endoscope to be able to display natural or desired colors of an imaged object.

In an endoscope, this has been achieved by performing color corrections, most commonly under the white-balance condition, i.e., the adjustment with respect to the point representing the color white on a chromatic diagram.

In a conventional endoscope, such color corrections can be carried out only outside of an internal organ of a patient inside of whom a scope is to be inserted for observations, prior to each diagnosis. In such a procedure, color corrections can be made only to lights from a light source of the system coming through the light guides of the scope.

However, color qualities of displayed images are affected by the state of the region surrounding the scope, and different reflection and absorption characteristics inside the human body tend to make displayed colors redder than the actual colors of the imaged objects. For example, the gastrointestinal parts or the duodenum are surrounded by the region with a red complexion, so the lights from the light source are affected by reflections and absorptions in the surrounding regions The lights coming off the region of interest within, such organs have a color temperature different from that for which the endoscope had been preadjusted.

Consequently, it was not possible in the prior art to achieve truly satisfactory reproductions of colors of the imaged object on the display.

SUMMARY OF THE INVENTION

It is therefore an object of the present invention to provide an endoscope capable of performing color corrections inside an internal organ where the actual observation occur thereby, achieving improved reproductions of colors of an imaged object on a display.

Another object of the present invention is to provide an endoscope which can facilitate verifications of correspondences between actual colors and displayed colors while a scope, an is inserted inside an internal organ.

According to one aspect of the present invention, there is provided an endoscope, comprising a scope, an imaging device means for imaging an object of interest in terms of electric signals, and white sheet means on its side wall which can be viewed by the imaging device means and which are wide enough to fill a single view of the imaging device means; camera control unit means for converting electric signals from the imaging device means into image signals; color correction unit means for performing color correction on image signals; and display means for displaying images of the object of interest. According to another aspect of the present invention, there is provided an endoscope, comprising a scope, an imaging device means for imaging an object of interest in terms of electric signals, and colored sheet means on its side wall which can be viewed by the imaging device means; camera control unit means for converting electric signals from the imaging device means into image signals; and display means for displaying images of the object of interest.

Other features and advantages of this invention will become apparent from the following description taken in conjunction with the accompanying drawings.

BRIEF DESCRIPTION OF THE DRAWINGS

FIG. 1 is a schematic block diagram of an endoscope according to one embodiment of the present invention.

FIG. 2 is an illustration of a scope of the endoscope shown in FIG. 1.

FIG. 3 is a detailed front end view of the scope shown in FIG. 2.

FIG. 4 (a) and (b) are illustrations of the extreme orientations of the top of the scope shown in FIG. 2.

DETAILED DESCRIPTION OF THE PREFERRED EMBODIMENTS

Referring now to FIG. 1, there is shown one embodiment of an endoscope according to the present invention comprising a scope 1 to be inserted in an internal organ including a charge coupled device (CCD)2 on its end for taking images of the object of interest; a system body 3 including a camera control unit (CCU)4 for converting signals from the CCD 2 into image signals, a light source 5 for generating illumination lights, a color correction unit 6 for performing color corrections on image signals, and a central processing unit (CPU)7 for controlling operations of the components of the system body 3; and a display 8 for displaying images taken.

Detailed view of the scope 1 of FIG. 1 is shown in FIG. 2 where the scope 1 further includes a solid head portion 10 at the end, a bendable portion 11 for turning the orientation of the solid head portion 10, a flexible middle portion 12 connected to the bendable portion 11, colored sheets 13 around the periphery of the flexible middle portion 12, a controller knob 14 for controlling vertical motions of the solid head portion 10, another controller knob 15 for controlling the horizontal motions of the solid head portion 10.

Detailed front end view of the solid head portion 10 of FIG. 2 is shown in FIG. 3 where it includes an object lens 16, light guides 17, a ventilation aperture 18, a water injection aperture 19, and a forceps insertion aperture 20.

The endoscope operates as follows: illumination lights from the light source 5 are shone on an object of interest through the light guides 17. The reflections of these illumination lights by the object are captured by the CCD 2 through the object lens 16. The CCD 2 produces electric signals representing the picture of the object which are converted into image signals by the CCU 4. Color corrections are performed on these image signals at the color correction unit 6, and color corrected images are displayed on the display 8. The operations of parts of the system body 3 are coordinated under the control of the CPU 7.

The solid head portion 10 of the scope 1 can be oriented to various directions by deflections of the bendable portion 11 controlled by the controller knobs 14 and 15, so that a wide field of view can be obtained. This is illustrated in FIG. 4, where FIG. 4(a) shows a vertical motion of the solid head portion 10 while FIG. 4(b) shows a horizontal motion of the solid head portion 10 by indicating its extreme positions. As can be seen in FIG. 4, the bendable portion 11 can be deflected by about 210° upwards, about 90° downwards, and about 100° sideways. So, with a sufficient upward deflection of the bendable portion 11, a part of the middle portion 12 can be viewed by the CCD 2.

According to the present invention, colored sheets 13 are placed on such a part of the middle portion 12 visible to the CCD 2. The colored sheets 13 may be comprised either of colored tapes attached to a side wall of the scope 1 or of a side wall of the scope 1 painted in colors. The colored sheets 13 have a white portion which is wide enough to fill most of a view of the CCD 2 at least at one orientation of the solid head portion 10, so that color corrections under the white-balance condition which requires a view mostly filled with white can be performed by orienting the solid head portion 10 in such a direction.

It can be seen that a portion of the colored sheets 13 in non-white color may be made wide enough to fill most of a view of CCD 2 so that the color corrections other than that under the white-balance condition can be performed.

It can also be seen that setting the solid head portion 10 to a particular orientation in order to prepare for the color correction as well as the process of the color corrections itself can be made automatic.

Meanwhile, the colored sheets 13 may have portions colored with various colors such as red, blue, green, etc. which can be used for verifications of correspondences between displayed colors and actual colors, i.e., comparison between the known actual colors of the colored sheets 13 and their appearances on the display 8. In this case, since widths of these portions of the colored sheets 13 are not restricted to be wide enough to fill an entire view of the CCD 2, they can be made into arbitrary sizes and shapes, so that they may be shaped to serve as scale markings for the length along the scope 1 simultaneously.

Moreover, many modifications and variations of this embodiment can be made without departing from the novel and advantageous features of this invention. Accordingly, all such modifications and variations are intended to be included within the scope of the appended claims.

What is claimed is:

1. An endoscope, comprising:
   a scope including a bendable viewing head portion, the top of which can be deflected to view a side wall of the scope;
   imaging device means at the top of the bendable head portion for imaging an object of interest in terms of electric signals;
   white sheets on the side wall which can be viewed by the imaging device means and which are wide enough to fill most of a single view of the imaging device means;
   camera control units means for converting electric signals from the imaging device means to image signals;
   color correction unit means for performing color correction on the image signals; and
   display means for displaying images of the object of interest.

2. The endoscope of claim 1, wherein the white sheets are comprised of white colored tapes attached on the side wall of the scope.

3. The endoscope of claim 1, wherein the white sheets are a portion of the side wall of the scope painted white.

4. An endoscope, comprising:
   a scope including a bendable viewing head portion, the top of which can be deflected to view a side wall of the scope;
   imaging device means at the top of the bendable head portion for imaging an object of interest in terms of electric signals;
   colored sheets on the side wall which can be viewed by the imaging device means;
   camera control unit means for converting electric signals from the imaging device means into image signals; and
   display means for displaying images of the object of interest.

5. The endoscope of claim 4, wherein the colored sheets are comprised of colored tapes attached on the side wall of the scope.

6. The endoscope of claim 4, wherein the colored sheets are comprised of a portion of the side wall of the scope painted in colors.

7. The endoscope of claim 4, wherein the colored sheets are in forms of scale markings for lengths along the scope.

8. The endoscope of claim 4, wherein the colored sheets are wide enough to fill most of a single view of the imaging device means, and which further include color correction unit means for performing color correction on image signals.

9. A color correcting endoscope, comprising:
   a scope portion for insertion into a body region, the scope portion having a sidewall and a bendable viewing end portion;
   color correcting indicia affixed to the sidewall of the scope portion;
   means for bending the end portion to a position at which the indicia can be viewed;
   means for converting the view of the body region to electrical signals;
   means for converting the electrical signals to visual images;
   means for color correcting the image signals on the basis of comparison to the color correcting indicia; and
   means for visually displaying the color corrected visual images.

10. The endoscope of claim 9, wherein the color correcting indicia are white sheets of sufficient size to take up most of a single view of the viewing end portion.

11. The endoscope of claim 9, wherein the color correcting indicia are colored sheets of sufficient size to take up most of a single view of the viewing end portion.

* * * * *